(12) United States Patent
Smith et al.

(10) Patent No.: US 6,506,553 B1
(45) Date of Patent: Jan. 14, 2003

(54) METHOD FOR DIAGNOSIS OF EPSTEIN-BARR VIRUS ASSOCIATED DISEASE

(75) Inventors: Richard S. Smith, Del Mar, CA (US); D. Elliot Parks, Del Mar, CA (US)

(73) Assignee: Ortho Diagnostics Systems, Inc., Raritan, NJ (US)

( * ) Notice: Subject to any disclaimer, the term of this patent is extended or adjusted under 35 U.S.C. 154(b) by 0 days.

(21) Appl. No.: 08/413,233

(22) Filed: Mar. 30, 1995

(51) Int. Cl.$^7$ .......................... C12Q 1/70; G01N 33/53; A61K 39/00; A61K 38/00

(52) U.S. Cl. .......................... 435/5; 435/7.1; 424/184.1; 424/186.1; 424/204.1; 424/230.1; 530/326

(58) Field of Search .................... 435/5, 7.1; 424/230.1, 424/184.1, 186.1, 204.1; 530/326

(56) References Cited

U.S. PATENT DOCUMENTS

| | | | |
|---|---|---|---|
| 3,654,090 A | 4/1972 | Schuurs et al. | 195/103.5 |
| 3,850,752 A | 11/1974 | Schuurs et al. | 195/103.5 R |
| 4,016,043 A | 4/1977 | Schuurs et al. | 195/103.5 R |
| 4,172,124 A | 10/1979 | Koprowski et al. | 424/85 |
| 4,196,265 A | 4/1980 | Koprowski et al. | 435/2 |
| 3,654,090 | 7/1982 | Schuurs et al. | 435/7 |
| 4,629,783 A | 12/1986 | Cosand | 530/324 |
| 4,879,213 A | * 11/1989 | Fox et al. | |

FOREIGN PATENT DOCUMENTS

| | | |
|---|---|---|
| EP | 0 173 254 | 3/1986 |
| EP | 0 280 813 | 9/1988 |
| EP | 0280813 | * 9/1988 |
| WO | WO 91/08224 | 6/1991 |
| WO | WO 94/06470 | 3/1994 |
| WO | WO 94/08597 | 4/1994 |

OTHER PUBLICATIONS

Fox et al. J. Clin. Lab. Analysis 1:140–145, 1987 (B).*
Pothen et al. Int. J. Cancer, 53:199–204, 1993.*
Jemmerson, Ronald. Immunological Recognition of Peptides in Medicine & Biology, Zegers, Boersma, Classen eds, CRC Press Inc., New York, Chapter 16, pp. 213–225, 1995.*
Eisenlohr et al., J. Exp. Med., 175:481–487, Feb. 1992.*
Young, Lawrence, In: Encyclopedia of Virology, Webster & Granoff eds. vol. 1, Academic Press, pp. 404–416, 1994.*
Ronald Jemmerson "Effects of Conformation, Amino Acid Sequence, and Carrier Coupling on the Immunological Recognition of Peptide and Protein Antigens" In: Immunological Recognition of Peptides in Medicine and Biology, Zegers, Boersma, and Claasen eds., CR, 1995.*
International Search Report Relating to EP 96911496.6.
Baer et al., DNA Sequence and Expression of the B95–8 Epstein Barr Virus Genome, Nature 310: 207–211 (Jul. 1984).
Basic and Clinical Immunology by D.P. Sites et al, Chapter 22 of the 4$^{th}$ Edition, published by Lange Medical Publications of Los Altos CA (1982).
Burton et al., "A Large Array of Human Monoclonal Antibodies to Type 1 Human Immunodeficiency Virus from Combinatorial Libraries of Asymptomatic Seropositive Individuals" Proc. Natl. Acad. Sci. USA vol. 88: 10134–10137 (Nov. 1991).
Coligan et al, Current Protocols in Immunology, Wiley Interscience, Units 12 and 2 (1991).

(List continued on next page.)

Primary Examiner—Hankyel T. Park
(74) Attorney, Agent, or Firm—Woodcock Washburn LLP

(57) ABSTRACT

A novel assay utilizing Epstein-Barr virus (EBV) specific peptides is disclosed. The assay is particularly useful for detecting early antigen antibodies in a blood sample from an individual having an EBV-associated disease, the disease preferably being infectious mononucleosis.

19 Claims, 5 Drawing Sheets

OTHER PUBLICATIONS

Current Protocols in Molecular Biology, Ausubel et al, eds. Wiley Interscience Press, (1989).
Curtiss, L.K. et al., "Localization of Two Epitopes of Apolipoprotein A–I That are Exposed on Human High Density Lipoproteins Using Monoclonal Antibodies and Synthetic Peptides", J. Biol. Chem., vol. 263, No. 27: 13779–13785 (Sep. 1988).
Diener et al., "Specific Immunosuppression by Immunotoxins Containing Daunomycin" Science vol. 231: 148–150 (Jan. 1986).
Dillner et al., "Antibodies Against a Synthetic Peptide Identify the Epstein–Barr Virus–Determined Nuclear Antigen" Proc. Natl. Acad. Sci USA 81: 4652–4656 (Aug. 1984).
Douillard, J.Y. and Hoffman, T., Basic Facts about Hybridomas, in Compendium of Immunology, vol. II, L. Schwartz, ed. (1981).
Douillard, J.Y. and Hoffman, "Monoclonal Antibodies Specific Immunotherapy of Gastrointestinal Tumors" T., Hybridoma 5 Supp 1: S139–S149 (Jul. 1986).
Eisenlohr et al., "Flanking Sequences Influence the Presentation of an Endogenously Synthesized Peptide to Cytotoxic T Lymphocytes" J. Exp Med. vol. 175: 481–487 (Feb. 1992).
Fox et al., "Synthetic Peptide Derived From the Epstein–Barr Virus Encoded Early Diffuse Antigen (EA–D)–Reactive with Human Antibodies" J. Clin. Lab. Anal. 1:140–145 (1987).
Greiner et al., "Recombinant Interferon Enhances Monoclonal Antibody–Targeting of Carcinoma Lesions in Vivo" Science vol. 235, No. 4791:895–898 (Feb. 1987).
Gull Laboratories, EBV–EA Test, Product No. EA100 (1988, Revised Jul. 1989).
Henle et al, "Epstein–Barr Virus Specific Diagnostic Tests in Infectious Mononucleosis" Human Pathology vol. 5, No. 5:551–565 (Sep. 1974).
Henle et al., "Demonstration of Two Distinct Components in the Early Antigen Complex of Epstein–Barr Virus–Infected Cells" Int. J. Cancer vol. 8, No. 3:272–282 (Nov. 1971).
Herlyn et al., "Anti–Idiotypic Antibodies Bear the Internal Image of a Human Tumor Antigen" Science vol. 232, No. 4746: 100–102 (Apr. 1986).
Hinuma, Y. et al., "Immunofluorescence and Herpes–Type Virus Particles in the P3HR–1 Burkitt Lymphoma Cell Line" J. Virol. vol. 1, No.5: 1045–1051 (Oct. 1967).
Jackman et al., "Expression of Epstein–Barr Virus gp350 as a Single Chain Glycoprotein for an EBV Subunit Vaccine" Vaccine 17: 660–668 (1999).
Kóhler and Milstein, "Continuous Cultures of Fused Cells Secreting Antibody of Predefined Specificity" Nature: vol. 256, No. 5517 495–497 (Aug. 1975).
Lenard, J. et al., "Use of Hydrogen Fluoride in Merrifield Solid–Phase Peptide Synthesis" J. Am. Chem. Soc. vol. 89, No. 1: 181–182 (Jan. 1967).
Lerner, "Tapping the Immunological Repertoire to Produce Antibodies of Predetermined Specificity" Nature 299: 592–596 (Oct. 1982).
Luka et al., "A Sensitive Enzyme–Linked Immunosorbent Assay (ELISA) Against the Major EBV–Associated Antigens. I. Correlation between ELISA and Immunofluorescence Titers Using Purified Antigens" J. Immunol. Methods 67: 145–156 (1984).
Merrifield, "Solid Peptide Synthesis. I. The Synthesis of A Tetrapeptide", J. Am. Chem. Soc. 85: 2149–2154 (Jul. 1963).
Oi et al., "Chimeric Antibodies", Bio Techniques vol. 4, No. 3: 214–221 (May/Jun. 1986).
Ortho Diagnostic Systems, Inc. ORTHO *Eptstein–Barr Virus EA(D+R)–IgG Antibody ELISA Test for Detection of IgG Antibodies to the Early Antigen (EA) Diffuse and Restricted (D&R) Components of the Epstein–Barr Virus (EBV), Product Code 520025, 1–38 (Draft revised Aug. 20, 1993).
Pearson et al., "Application of Epstein–Barr Virus (EBV) Serology to the Diagnosis of Nort American Nasopharyngeal Carcinoma" Cancer 51: 260–268 (Jan. 1983).
Pearson et al. "Identification of an Epstein–Bar Virus Early Gene Encoding a Second Component of the Restricted Early Antigen Complex" Virology 160: 151–161 (1987).
Pothen et al., "Identification of T– and B–Cell Epitopes Associated with a Restricted Component of the Epstein–Barr Virus–Induced Early Antigen Complex" Int. J. Cancer 53: 199–204 (1993).
Pothen et al., "Human T–Cell Recognition of Epstein Barr Virus–Induced Replication Antigen Complexes" Int. J. Cancer 49: 656–660 (1991).
Rhodes et al., "Human Immune Responses to Synthetic Peptides from the Epstein–Barr Nuclear Antigen" J. Immunol vol. 134, No. 1: 211–216 (Jan. 1985).
Smith et al., "Antibodies to an Epstein–Barr Virus Nuclear Antigen Synthetic Peptide in Infectious Mononucleosis" Am. J. Clin. Pathology vol. 92 No. 4: 447–451 (Oct. 1989).
Spira et al., "The Identification of Monoclonal Class Switch Variants by Sib Selection and an ELISA Assay" J. Immunol. Methods 74: 307–315 (1984).
Steplewski et al., "Isolation and Characterization of Anti–Monosialoganglioside Monoclonal Antibody 19–9 Class–Switch Variants" Proc. Natl. Acad. Sci., USA, vol. 82: 8653–8657 (Dec. 1985).
Stewart and Young, "Laboratory Techniques in Solid Phase Peptide Synthesis" Solid Phase Peptides Synthesis (W. H. Freeman & Company, San Francisco, Chapter 2 pp. 27–64 (1969).
Sun et al., "Chimeric Antibodies with 17–1A–Derived Variable and Human Constant Regions" Hybridoma, vol. 5 Supplement 1: S17–S20 (1986).
Sutcliffe et al., "Antibodies That React With Predetermined Sites on Proteins" Science vol. 219, No. 4585 660–666 (Feb. 1983).
Tainer et al, "The Reactivity of Anti–Peptide Antibodies is a Function of the Atomic Mobility of Sites in a Protein" Nature 312: 127–134 (Nov. 1984).
Ulaeto et al, "In Vitro I Cell Responses to a Candidate Epstein–Barr Virus Vaccine: Human CD 4+ T–Cell Clones Specific for the Major Envelope Glycoprotein gp340" Eur. J. Immunol. 18: 1689–1697 (1988).
Waldmann, "Monoclonal Antibodies in Diagnosis and Therapy" Science 252: 1657–1662 (Jun. 1991).
Wolff et al, "The Use of Monoclonal ANTI–Thy$_1$ IgG$_1$ for the Targeting of Liposomes to AKR–A Cells in Vitro and in Vivo" Biochemica et Biophysica Acta, 802: 259–273 (1984).
Young "Epstein–Barr Virus" Encyclopedia of Virology, vol. 1, Edited by Webster and Granoff, Academic Press, 404–416 (1994).

* cited by examiner

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 15 amino acids
      (B) TYPE: amino acid
      (C) STRANDEDNESS: single -continued

```
        (D) TOPOLOGY: linear (ii) MOLECULE TYPE: peptide (ix) FEATURE:
        (A) NAME/KEY: Peptide
        (B) LOCATION: 1..15

(xi) SEQUENCE DESCRIPTION: SEQ ID NO:1:

Lys Gln Lys His Pro Lys Lys Val Lys Gln Ala Phe Asn Pro Leu
1               5                   10                  15

(2) INFORMATION FOR SEQ ID NO:2:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..13

(xi) SEQUENCE DESCRIPTION: SEQ ID NO:2:

Pro Ala Arg Pro Glu Thr Pro Ser Pro Ala Ile Pro Ser
1               5                   10

(2) INFORMATION FOR SEQ ID NO:3:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..16

(xi) SEQUENCE DESCRIPTION: SEQ ID NO:3:

Glu Thr Phe Thr Glu Thr Trp Asn Arg Phe Ile Thr His Thr Glu Tyr
1               5                   10                  15
```

METHOD FOR DIAGNOSIS OF EPSTEIN-BARR VIRUS ASSOCIATED DISEASE

BACKGROUND OF THE INVENTION

1. Field of the Invention

This invention relates to Epstein-Barr virus (EBV) associated disease, and specifically to the use of EBV specific peptides for diagnosis of EBV-associated disease.

2. Description of Related Art

Epstein-Barr virus (EBV) is a human herpesvirus which is endemic in all human populations. Most people are infected with the virus in early childhood and then carry the virus for life. If the initial infection is delayed until adolescence, infectious mononucleosis (IM) frequently results. IM is a self-limiting symptomatic disease with illness ranging from mild to severe. EBV is also linked with certain kinds of cancer. In the malarial belt of Africa, EBV is a contributory factor in the development of Burkitt's lymphoma (BL) and in South-East Asia, the virus is linked to the high incidence of undifferentiated nasopharyngeal carcinomas (NPC). EBV has also been shown to be associated with certain malignancies occurring in organ transplant recipients and in some patients with acquired immune deficiency syndrome (AIDS).

Acute viral infection leads to the production of specific nuclear antigens (termed EBNA-I and EBNA-II), an "early antigen" (EA) complex, viral capsid antigens (VCA), and other associated molecules. The "early antigen complex" consists of the "early antigen-diffuse" (EA-D) and the "early antigen-restricted" (EA-R) antigens, based on their distribution in immunofluorescence assays. The antigens are distinguished by being localized in the cytoplasm plus nucleus (i.e. diffuse distribution) or in the cytoplasm only (i.e. restricted) and by their staining appearance in methanol-fixed cells. These EA antigens, with molecular weight 50–55 Kd, 17 Kd, and 85 Kd, respectively, are synthesized during the "lytic" phase of EBV infection and not in transformed lymphoblastoid cells. Antibodies reactive with the early antigens are present during acute EBV infection and then disappear as the virus enters a phase of latency. The reappearance of anti-EA antibodies signals viral reactivation and provides some insight to the possible role of this virus in diseases such as nasopharyngeal carcinoma and Burkitt's lymphoma.

Indirect evidence has suggested a possible role for EBV reactivation in patients with Sjogren's syndrome, an autoimmune disorder characterized by lymphoid infiltrates of the salivary gland (the normal site for EBV latency). Since antibodies to EA antigens are detected by immunofluorescence assays, such antibodies cannot be detected in patients who possess antinuclear and anticytoplasmic antibodies as part of an autoimmune disease. Therefore it would be desirable to have an assay which uses purified EA molecules to allow measurement of anti-EA antibodies in patients with autoimmune diseases and to more accurately quantitate anti-EA antibodies in other patients with acute or reactivated EBV.

Recently, the DNA sequence of EBV was determined (Baer, et al., *Nature* 310:207, 1984) and the EA-D antigen localized in the genome. Using a monoclonal antibody directed against the EA-D protein, sufficient protein was purified to allow partial amino acid sequence determination and thus localization of the coding sequences. Using that information, it was possible to prepare a series of synthetic peptides based on the DNA sequence. The same strategy has proved useful in identifying immunologically important epitopes on the EBNA-I antigen (Rhodes, et al., *J. Immunol.*, 134:211, 1985) and the EBNA-II antigens (Dillner, *J. Proc. Natl. Acad. Sci.* U.S.A., 81:4652, 1984) of EBV. A synthetic peptide derived from the EA-D molecule which contains an epitope reactive with immune human sera from patients with IM and other disease states has also been described (Fox, et al., *J. Clin. Lab. Anal.*, 1:140, 1987).

Recent studies have shown that chemically synthesized polypeptides corresponding to short linear segments of a protein's primary amino acid residue sequence can be used to induce antibodies that immunoreact with the native protein (Lerner, et al., *Nature*, 299:592, 1982; Sutcliffe, et al., *Science*, 219:260, 1983). In addition, some studies have shown that synthetic polypeptides can immunoreact with antibodies induced by native proteins (Rhodes, et al., *J. Immunol.*, 134:211 1985). Thus, some synthetic polypeptides can immunologically mimic the immunogenic and antigenic determinants of native proteins.

Previous studies have examined the cellular immune response to EBV-induced antigens synthesized during the virus replication cycle (Pothen, et al., *Int. J. Cancer*, 49:656, 1991). The results demonstrated that some of the components of the early antigen (EA) complex were very effective in inducing a strong T-cell proliferative response similar to that previously noted with the major membrane glycoprotein, gp350/250 (Ulaeto, et al., *Europ. J. Immunol.*, 18:1689, 1988). Both CD4+ and CD8+ lymphocyte populations from EBV-infected donors proliferated in the presence of polypeptides purified from the EA complex by immunoaffinity chromatography. The major polypeptide of EA-D and one of the major poly-peptides of EA-R were particularly effective in this T-cell recognition assay. The data suggested that these components of the EA complex might function as important target antigens in the immunosurveillance of EBV-infected or immortalized cells. Identification of the dominant T and B-cell epitopes expressed on EA-R complex polypeptides would provide information on the importance of the antibody responses to these components in the diagnosis and management of individuals with EBV-associated lymphoproliferative diseases.

The heterophile antibody test is currently the most widely used procedure for the diagnosis of acute IM. It is positive in 85–90% of adolescents and young adults, and a smaller amount of children with primary EBV infection. Specific EBV serology can be used to differentiate the heterophile-negative infections from mononucleosis-like illnesses caused by other agents including cytomegalovirus (CMV), human immunodeficiency virus (HIV), *Toxoplasma gondii* and adenovirus. Tests for individual measurements of antibodies to several different EBV-specific antigens, including the viral capsid antigen (VCA), EA-R, EA-D, and nuclear antigen (EBNA) have been described. In addition, differentiation of the IgG and IgM subclasses of the VCA can be helpful in diagnosis of EBV-associated disease. In heterophile negative serum, demonstration of the presence of VCA IgM and transient levels of early antigen antibodies may be considered diagnostic for acute IM.

About 80% of IM patients demonstrate a rise in antibodies to EA-D IgG during the acute phase of IM which may. then persist through the convalescent phase. EA-R antibodies appear transiently during the late convalescent phase, although young children and asymptomatic adults may exhibit an increase in antibodies during the acute phase. Early antigen IgG antibodies may persist for several months or even years following acute infection. Antibodies to EA are also seen in BL, NPC and in some cases of reactivated EBV infection. High levels of EA-R antibodies are generally seen only in the case of BL.

Although screening assays for detection of IM have been described, they do not identify as many as 10% of those patients with IM (U.S. Pat. No. 4,879,213, which utilizes K7B peptide). It would be desirable to develop improved methods to assay for the presence of EA-R or EA-D and anti-EA-R or anti-EA-D antibodies in a body sample so as to allow diagnosis of EBV involvement in disease, as well as diagnosis of the stage of disease, with greater sensitivity than already existing assays. It is also desirable to develop a means for distinguishing between EA IgG and IgM levels in order to identify acute versus convalescent phases of EBV-associated diseases, such as IM.

SUMMARY OF THE INVENTION

The present invention provides a simple and reliable diagnostic assay for detection of IgG and IgM antibodies to the diffuse (EA-D) and restricted (EA-R) components of the early antigen of the Epstein-Barr virus (EBV) in blood, and more specifically in serum. This novel assay can be used for diagnosis of EBV-associated disease; such as infectious mononucleosis (IM) for example, and can also be utilized to distinguish between individuals in the acute versus the convalescent phase of disease. The assay described herein is useful for detecting such EBV-associated diseases as IM with increased sensitivity over existing methods.

DETAILED DESCRIPTION OF THE INVENTION

Figure 1:
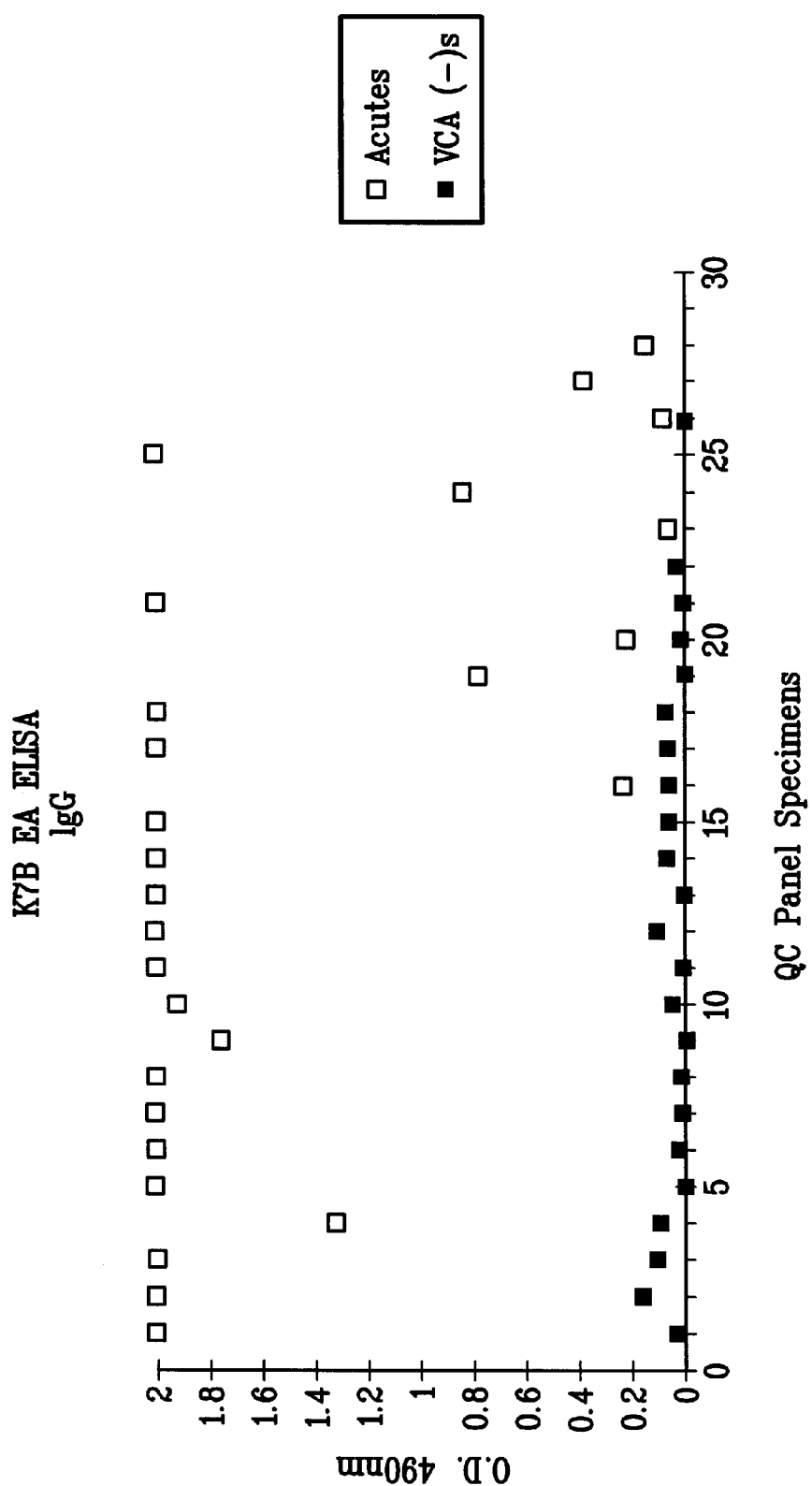
FIG. 1 shows the results of an ELISA utilizing K7B EA peptide in acute and VCA negative (control) serum detection of IgG antibody is shown.
Figure 2:
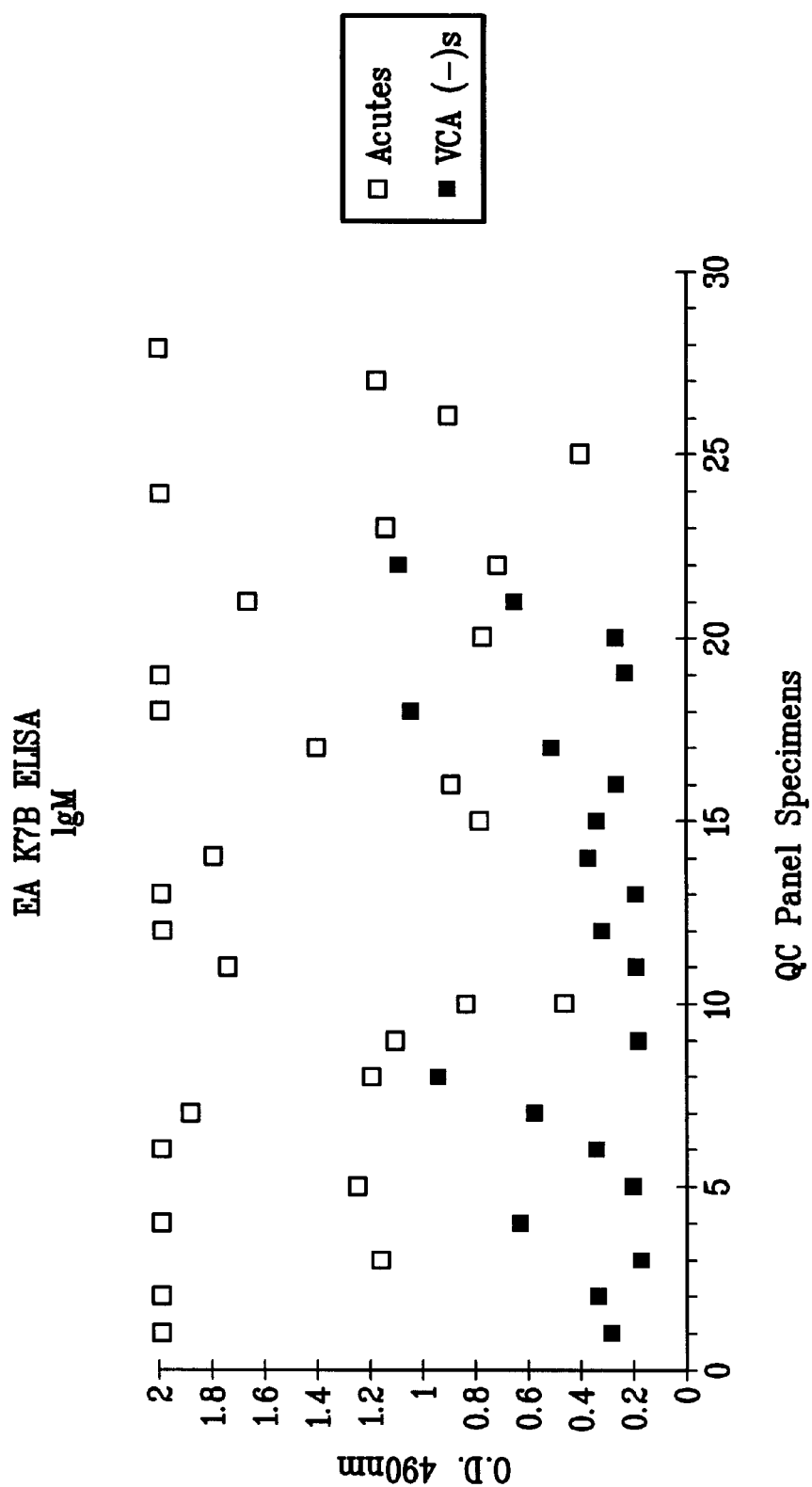
FIG. 2 shows the results of an ELISA utilizing K7B EA peptide in acute and VCA negative (control) serum detection of IgM antibody is shown.

The present invention provides an assay for the presence and quantification of anti-EA antibodies associated with an EBV-associated disease in a specimen from an individual. Preferably, the method of the invention is used for diagnosis of infectious mononucleosis (IM) and the preferred individual is a human.

In a preferred embodiment, the present invention provides a method for detecting antibodies which bind to a peptide having the amino acid sequence [XKQKHPKKVKQAFNPLY]$_n$ or [XPARPETPSPAIPS]$_n$, wherein X and Y are independently from about 0 to 5 naturally occurring amino acids, wherein n is about 1 to 1000, and wherein the peptide is capable of binding antibody in a specimen from an individual with Epstein-Barr virus (EBV) associated disease. The method comprises contacting a specimen from the individual with the peptides, incubating the specimen and the peptides for a period of time and under conditions sufficient for the antibodies to bind to the peptides, and detecting the presence of the antibodies to the peptides.

The method of the invention comprises the epitopic polypeptides KQKHPKKVKQAFNPL (SEQ ID NO:1) and PARPETPSPAIPS (SEQ ID NO:2), and conservative variations and mixtures of these peptides. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide. Thus, by using a routine screening method, such as by testing a conservative variant polypeptide with sera from a patient with EBV-associated disease, one of skill in the art can readily determine if the variant polypeptide has the requisite biological activity of the polypeptide of the invention without resort to undue experimentation.

The method of the invention further includes the addition of the polypeptide ETFTETWNRFITHTEY (SEQ ID NO:3) to polypeptides KQKHPKKVKQAFNPL (SEQ ID NO:1) and PARPETPSPAIPS (SEQ ID NO:2), for diagnosis of between 95% and 100% of IM patients. SEQ ID NO:1 is the 50.10 peptide of EA-D, SEQ ID NO:2 is the K7B peptide of EA-D (U.S. Pat. No. 4,879,213) and SEQ ID NO:3 is the 17.1 peptide of EA-R. Reactivity of a sample with EA-D, 50.10 peptides or anti-EA-D peptide antibodies is preferably associated with infectious mononucleosis and nasopharyngeal carcinoma. Likewise, reactivity with EA-R, 17.1 peptides or anti-EA-R peptide antibodies is preferably associated with lymphonias. These specific peptides and their corresponding monoclonal antibodies are also useful for detecting the EA-D and EA-R transitions associated with a particular disease state.

The epitopic polypeptides of the invention may contain additional amino acids at the amino and carboxy termini in order to increase their serological reactivity. Preferably, the additional amino acids are the naturally occurring amino acids of the protein, or conservative variations of these amino acids, and range in number from about 0 to about 5 independently. For example, a variation of SEQ ID NO:1 comprises the epitopic polypeptide, ARQKQKHPKKVKQAFNPLI, wherein the underlined amino acids represent extensions of the original polypeptides. The polypeptides of the invention can also be utilized as repeating units ranging from 1 to about 1000 units in length. These units can be homogeneous, for example, where all of the units are repeats of the same polypeptide or can be mixtures of the polypeptides of the invention.

The peptides used in the method of the invention can be used singularly, in mixtures, or as multimers such as aggregates, polymers, and the like, in various combinations. Thus, the invention embraces polypeptides which comprise one or more of the same, or different, polypeptides of the invention to produce a homogeneous or heterogeneous polymer with respect to the particular polypeptides of the invention which are contained therein. Appropriate techniques for producing various mixtures, aggregates, multimers and the like will be known to those of skill in the art. For example, the invention includes a polypeptide comprising SEQ ID NO:1 and SEQ ID NO:2, and optionally SEQ ID NO:3, or any combination of these, wherein the sequences may be linked either directly or indirectly, for example, by using a spacer or linker moiety.

Peptides of the invention can be synthesized by such well known solid phase peptide synthesis methods described by Merrifield, *J. Am. Chem. Soc.* 85:2149, 1962, and Stewart and Young, *Solid Phase Peptides Synthesis*, (Freeman, San Francisco, 1969, pp. 27–62), using a copoly(styrene-divinylbenzene) containing 0.1–1.0 mMol amines/g polymer. On completion of chemical synthesis, the peptides can be deprotected and cleaved from the polymer by treatment with liquid HF-10% anisole for about ¼–1 hours at 0° C. After evaporation of the reagents, the peptides are extracted from the polymer with 1% acetic acid solution which is then lyophilized to yield the crude material. This can normally be purified by such techniques as gel filtration on SEPHADEX G-15 using 5% acetic acid as a solvent. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy, molar rotation, solubility, and quantitated by the solid-phase Edman degradation.

During or after the synthesis, reactive amino acids may be protected by various blocking groups, for example, cysteines may be blocked by 3,4-dimethylbenzyl (DMB) groups, arginines and histidines by tosyl (TOS) groups, aspartic acid and glutamic acids by benzyl (Bzl) groups, and lysines the 2-chloro-benzyloxycarboxyl (2-CBZ) groups. Other protective blocking groups are well-known, and can be used in the present invention. Those of ordinary skill in the art will know of other techniques for peptide synthesis, or can readily ascertain such techniques, without resorting to undue experimentation.

The term "EBV-associated disease" means any disease caused, directly or indirectly, by EBV as well as diseases which predispose a patient to infection by EBV. Examples of diseases falling into the former category include infectious mononucleosis, nasopharyngeal carcinoma, and Burkitt's lymphoma. Diseases in the latter category (i.e., those which place the patient at risk of EBV infection) include Sjorgren's syndrome and, generally, any condition that causes a state of immunosuppression or decreased function of the immune system such as patients who receive organ transplants and certain cancer therapies.

The peptides described herein are suited for use, for example, in immunoassays in which they can be utilized in liquid phase or bound to a solid phase carrier. In addition, the peptides in these immunoassays can be detectably labeled in various ways. Alternatively, a detectably labeled protein which binds to antibody can be utilized to detect binding of the peptide and EA-D or EA-R antibody. For example, a preferred detectably labeled protein is a second antibody which specifically binds to IgM, IgG, or IgA antibody.

Examples of types of immunoassays which can be utilized in the invention are competitive and non-competitive immunoassays in either a direct or indirect format. Examples of such immunoassays are the radioimmunoassay (RIA) and the sandwich (immunometric) assay. Detection of the antibodies using the peptides of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

There are many different labels and methods of labeling known to those of ordinary skill in the art. Examples of the types of labels which can be used in the present invention: include enzymes, radioisotopes, fluorescent compounds, colloidal metals, chemiluminescent compounds, phosphorescent compounds, and bioluminescent compounds. Those of ordinary skill in the art will know of other suitable labels for binding to the peptides or second antibody for example, or will be able to ascertain such, using routine experimentation. Furthermore, the binding of these labels to the peptides of the invention or a second antibody can be done using standard techniques common to those of ordinary skill in the art.

"ELISA" refers to an enzyme-linked immunosorbent assay that employs an antibody or antigen bound to a solid phase and an enzyme-antigen or enzyme-antibody conjugate to detect and quantify. the amount of an antigen present in a sample. (A description of the ELISA technique is found in Chapter 22 of the 4th Edition of *Basic and Clinical Immunology* by D. P. Sites, et al., published by Lange Medical Publications of Los Altos, Calif. in 1982 and in U.S. Pat. Nos. 3,654,090; 3,850,752; and 4,016,043, which are all incorporated herein by reference.)

For an ELISA, typically used enzymes linked to a polypeptide as a label include horseradish peroxidase, alkaline phosphatase and the like. Each of those enzymes is used with a color-forming reagent or reagents (substrate) such as hydrogen peroxide and o-phenylenediamine; and p-nitrophenyl phosphate, respectively. Alternatively, biotin linked to a polypeptide can be utilized as a label to signal the presence of the immunoreactant in conjunction with avidin that is itself linked to a signalling means such as horseradish peroxidase.

For purposes of the invention, an anti-EA-D or anti-EA-R antibody specific for a peptide of the invention may be detected by the method of the invention when present in biological fluids and tissues. Any specimen containing a detectable amount of such antigen can be used. A sample can be a liquid such as urine, saliva, cerebrospinal fluid, blood, serum and the like, or a solid or semi-solid such as tissues, feces, and the like, or, alternatively, a solid tissue such as those commonly used in histological diagnosis. An especially preferred sample is blood, and most preferably serum. Preferably, the specimen is a human blood or serum sample.

The specific concentrations of the antibody and antigen, the temperature and time of incubation, as well as other assay conditions, can be varied, depending on such factors as the concentration of the antibody in the sample, the nature of the sample and the like. Those of skill in the art will be able to determine operative and optimal assay conditions for each determination by employing routine experimentation. Typically, the time period is predetermined for a given set of reaction conditions by well known methods prior to performing the assay.

For example, the immunoassay of the invention may be run at 4°–45° C. Under biological assay conditions, the maintenance time period is usually from minutes to hours, such as 30 minutes to 2 hours to overnight, however, these time periods will vary. Other steps such as washing, stirring, shaking, filtering, or pre-assay extraction of antigen, and the like, may, of course be added to the assay, as may be desired or necessary for a particular situation. The immunocomplex formed can then be detected by means described herein.

The method of the invention is well suited for preparation of a diagnostic kit for detecting anti-EA antibodies in a specimen. Therefore, in another embodiment, the invention provides a diagnostic kit for detecting the presence of antibodies which bind to a peptide having the amino acid sequence [XKQKHPKKVKQAFNPLY]$_n$ or

[XPARPETPSPAIPSY]$_n$, wherein X and Y are independently from about 0 to 5 naturally occurring amino acids, wherein n is about 1 to 1000, and wherein the peptide is capable of binding antibody in a specimen from an individual with Epstein-Barr virus (EBV) associated disease. The kit comprises a first container containing the peptide(s) and a second container containing a detectable label for detecting binding of the peptides and the antibodies. The kit may further include a container comprising a peptide having the amino acid sequence [XETFTETWNRFITHTEYY]$_n$.

A kit of the invention comprises a carrier means being compartmentalized to receive in close confinement one or more container means such as vials, tubes, and the like, each of the container means comprising one of the separate elements to be used in the method. For example, one of the container means may comprise the peptides of the invention which are or can be, detectably labelled. The kit may also have containers containing any of the other above-recited immunochemical reagents used to practice the diagnostic methods.

The diagnostic system or kit described herein can also include, preferably as a separate package, a specific binding agent. A "specific binding agent" is a molecular entity capable of selectively binding a reagent species of the present invention or a complex containing such a species, but is not itself a polypeptide or antibody molecule composition of the present invention. Exemplary specific binding agents are second antibody molecules, complement proteins or fragments thereof, S. aureus protein A, and the like. Preferably, the specific binding agent binds the reagent species when that species is present as part of a complex and most preferably, the binding agent is an IgG or IgM antibody or antibody binding fragment. In preferred embodiments, the specific binding agent is labeled.

The diagnostic kit of the present invention can be used in an "ELISA" format to detect the quantity of an EA antibody in a vascular fluid sample, such as blood, serum, or plasma. Thus, a K7B and 50.10 peptide of the present invention, alone or in combination with a 17.1 peptide, can be affixed to a solid matrix to form a solid support that comprises a package in the subject diagnostic systems. A reagent is typically affixed to a solid matrix by absorption from an aqueous medium although other modes of affixation applicable to proteins and polypeptides well known to those skilled in the art, can be used.

The peptides described for use in the method of the invention can be bound to many different carriers and used to detect the presence of an antigen comprising a polypeptide of the invention. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding peptides, or will be able to ascertain such, using routine experimentation.

Useful solid matrices are also well known in the art. Such materials are water insoluble and include cross-linked dextran available under the trademark SEPHADEX from Pharmacia Fine Chemicals (Piscataway, N.J.); agarose; beads of polystyrene beads about 1 micron to about 5 millimeters in diameter available from Abbott Laboratories of North Chicago, Ill.; polyvinyl chloride, polystyrene, cross-linked polyacrylanide, nitrocellulose- or nylon-based webs, such as sheets, strips or paddles; or tubes, plates or the wells of a microtiter plate such as those made from polystyrene or polyvinylchloride.

The reagent species or labeled specific binding agent of a diagnostic kit described herein can be provided in solution, as a liquid dispersion or as a substantially dry power, e.g., in lyophilized form. Where the indicating means is an enzyme, the enzyme's substrate can also be provided in a separate package of a system. A solid support, such as the before-described microtiter plate and one or more buffers can also be included as separately packaged elements in this diagnostic assay system.

The packaging materials discussed herein in relation to diagnostic systems are those customarily utilized in diagnostic systems. The term "package" refers to a solid matrix or material, such as glass, plastic (e.g., polyethylene, polypropylene and polycarbonate), paper, foil and the like capable of holding within fixed limited a diagnostic reagent such as a peptide or second antibody of the present invention. Thus, for example, a package can be a bottle, vial, plastic and plastic-foil laminated envelope or the like container used to contain a contemplated diagnostic reagent or it can be a microtiter plate well to which microgram quantities of a contemplated diagnostic reagent have been operatively affixed, i.e., linked so as to be capable of being immunologically bound by an antibody or polypeptide to be detected.

The above disclosure generally describes the present invention. A more complete understanding can be obtained by reference to the following specific examples which are provided for purposes of illustration only, and are not intended to limit the scope of the invention.

EXAMPLES

The following Examples describe a novel ELISA assay which detects antibody to Epstein-Barr virus early antigen from patients with infectious mononucleosis. The ELISA contains synthetic peptides from the EA reading frames BMRF1. (EA-D p50/52) and BHRF1 (EA-R p17) (U.S. Pat. No. 4,879,213).

Example 1

Identification of Infectious Mononucleosis Patients

Serum samples from patients with IM were assayed for the presence of anti-EA-D antibodies using the ELISA described below. The sera assayed were from patients who were diagnosed as having acute infectious mononucleosis (IM), based on their clinical features (atypical lymphocytes) (Henle, et al., *Human Pathology*, 5:551–565, 1974) and a positive sheep red blood cell agglutination (i.e., heterophile). To confirm the IM diagnosis, sera from these groups were examined for EBNA-1 and anti-VCA antibodies (by IFA; Henle, et al., i Int. J. Cancer, 8:272, 1971) (TABLE 1). Samples which qualified as IM positive were confirmed by Western blot analysis (Smith, et al., *Am. J. Clin. Pathology*, 92:447–451, 1989) as 50–55K positive (see Coligan, et al., *Current Protocols in Immunology*, Wiley Interscience, 1994, Unit 12). Twenty-eight of thirty-six patients were Western blot positive for EA-D (50–55 kD) and utilized as test samples in the assays described herein.

TABLE 1

INFECTIOUS MONONUCLEOSIS SAMPLE QUALIFICATION PANEL

| CATEGORY | NUMBER | HETEROPHIL (NO. +) | HEMATOLOGY[1] | VCA IFA (NO. +) | EBNA-ACIF (NO. +) |
|---|---|---|---|---|---|
| ACUTE MONO | 36 | 36 | 30 | 36 | 0 |
| VCA-[2] | 22 | 0 | 0 | 0 | 0 |
| CONVALESCENT | 12 | 0 | 0 | 12 | 100 |

[1]number with atypical lymphocytes (>8%)
[2]VCA negative patients presumably had not undergone primary EBV infection and were the control group. VCA positive patients had probably been exposed to EBV.

Example 2

ELISA Assay for Anti-EA-D and Anti-EA-R Antibody

ELISA was carried out by standard techniques known in the art (Coligan, et al., supra, Unit 2; Luka, et al., *J. Immunol Meth.*, 67:145, 1984). Synthetic peptides diluted in 0.5 M $Na_2CO_3$ buffer, pH 9.5, were affixed to the wells of a microtiter plate (Linbro) as a matrix. Approximately 5 µg of EA-D peptide K7B (PARPETPSPAIPS), 2.5 µg of EA-D peptide 50.10 (KQKHPKKVKQAFNPL) and 0.01 µg of EA-R peptide 17.1 (ETFTETWNRFITHTE) were added to the plates and incubated overnight at 4° C. Following this incubation period, the plates were washed 5x with Tris-HCl, pH 7.4, containing 0.05% Tween 20, 50 mM NaCl and 100 mg per liter albumin (Sigma) and dried for 20 minutes at room temperature. The plates were screened with different anti-EA-R or EA-D antibody positive human sera and the monoclonal antibody to p17 or p50 to identify the optimal concentration of antigen to be used in the serological studies. Alkaline-phosphatase-labelled goat anti-human IgG or IgM (Sigma) or goat anti-mouse IgG or IgM (Sigma) was used as the indicator system.

For the testing of human sera for antibodies to the synthetic peptides, sera were diluted 1:10 in ELISA buffer, added in 0.1 ml volumes to wells coated with optimal concentrations of antigen and the plates were incubated for 60 minutes at room temperature. After 4 washes with ELISA buffer, 100 µl of alkaline phosphatase-labelled goat anti-human IgG or IgM in ELISA buffer were added to each well and the plates were incubated at room temperature for 1 hour. Following four more washes in buffer, the enzyme reaction was performed by dissolving 1 mg per ml of Sigma alkaline phosphatase substrate in 1M diethanolamine buffer, pH 10.4, containing 1 mM $MgCl_2$ and 0.1 mM $ZnCl_2$, and 100 µl of the mixture was then added to each well. The reaction was allowed to proceed for 30 minutes at 37° C. and then the plates were screened directly with a microplate reader, TITERTEK MULTISKAN MC (Flow), at 420 nm. Readings above 0.10, which was 2x the background noted with antibody-negative sera, were considered positive reactions.

Example 3

Sensitivity of EA-D and EA D+R Peptide ELISAS for Detection of Infectious Mononucleosis The ELISA assay as described in Example 1 was utilized to determine the sensitivity of the K7B, 50.1 and 17.1 peptide alone, and K7B in combination with 50.10 or in combination with both 50.10 and 17.1 peptide, for detecting IM in a serum sample. The results of the peptide ELISAS are shown in Tables 2–5 respectively, and Table 6 summarizes the results. Not only did the combination of peptides identify up to 100% of IM positive samples, but it was also able to distinguish between IgG and IgM isotypes.

Of the three samples testing negative for IgG with K7B alone (Table 2, #13769 and 14128) two tested positive when K7B and 50.1 peptides were used in combination (Table 4). In addition, sample #14043, which tested negative for IgM with K7B alone (Table 2) tested positive when K7B and 50.1 peptides were used (Table 4).

The results of these assays are also shown in the plots in FIGS. 1–4. The data shown in FIGS. 1 and 2 demonstrate that the EA-D peptide K7B ELISA can separate several of the EA-D positive samples from the control group (VCA−). The data in FIG. 1 confirm that the K7B ELISA can also be used to detect EA in mononucleosis samples compared to the control group. However, the K7B IgM ELISA (FIG. 2) did not discriminate as well between the two groups.

Figure 3:
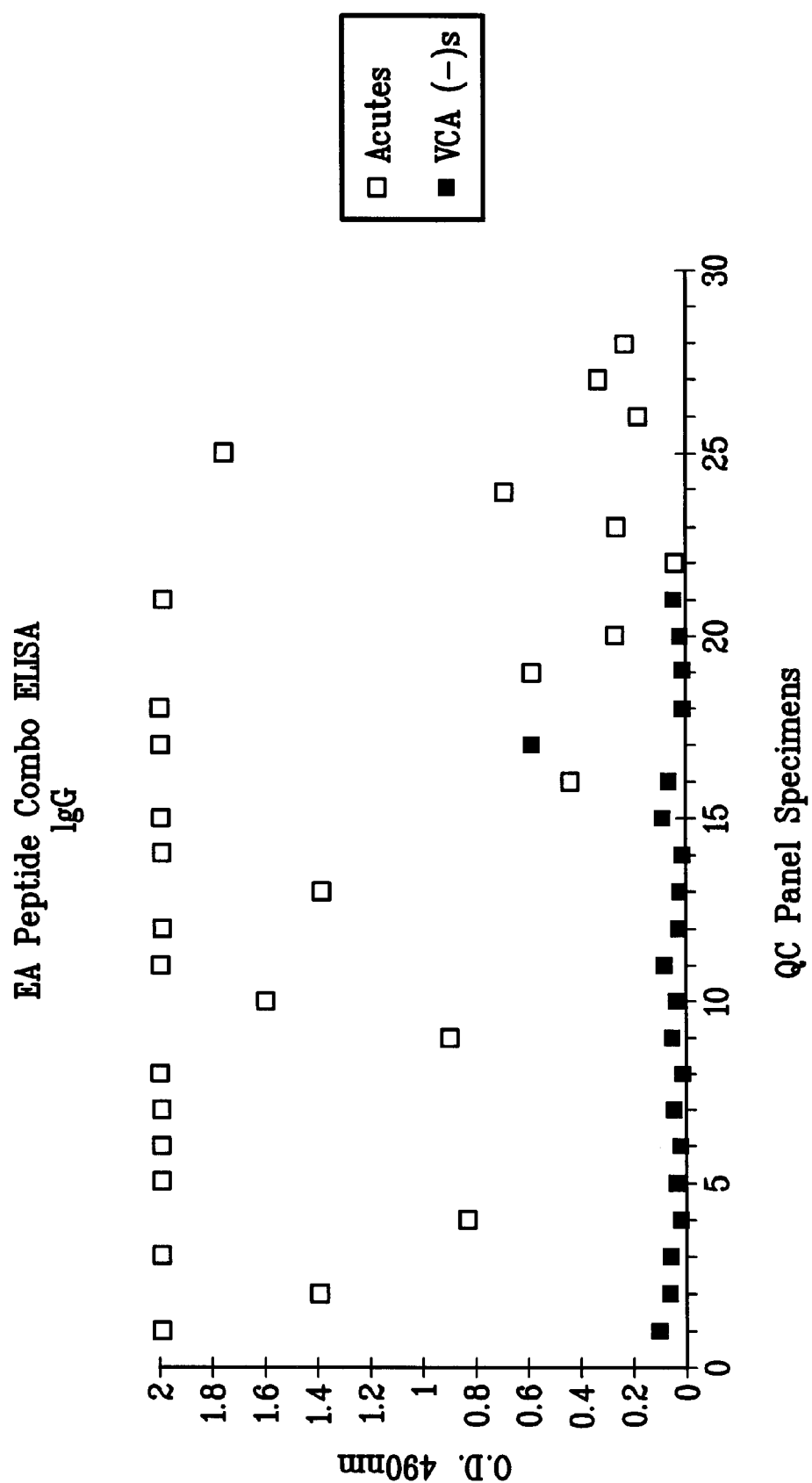
FIG. 3 shows an EA peptide combination ELISA (K7B, 50.10, 17.1). Detection of IgG antibody is shown for acute and VCA negative (control) serum.
Figure 4:
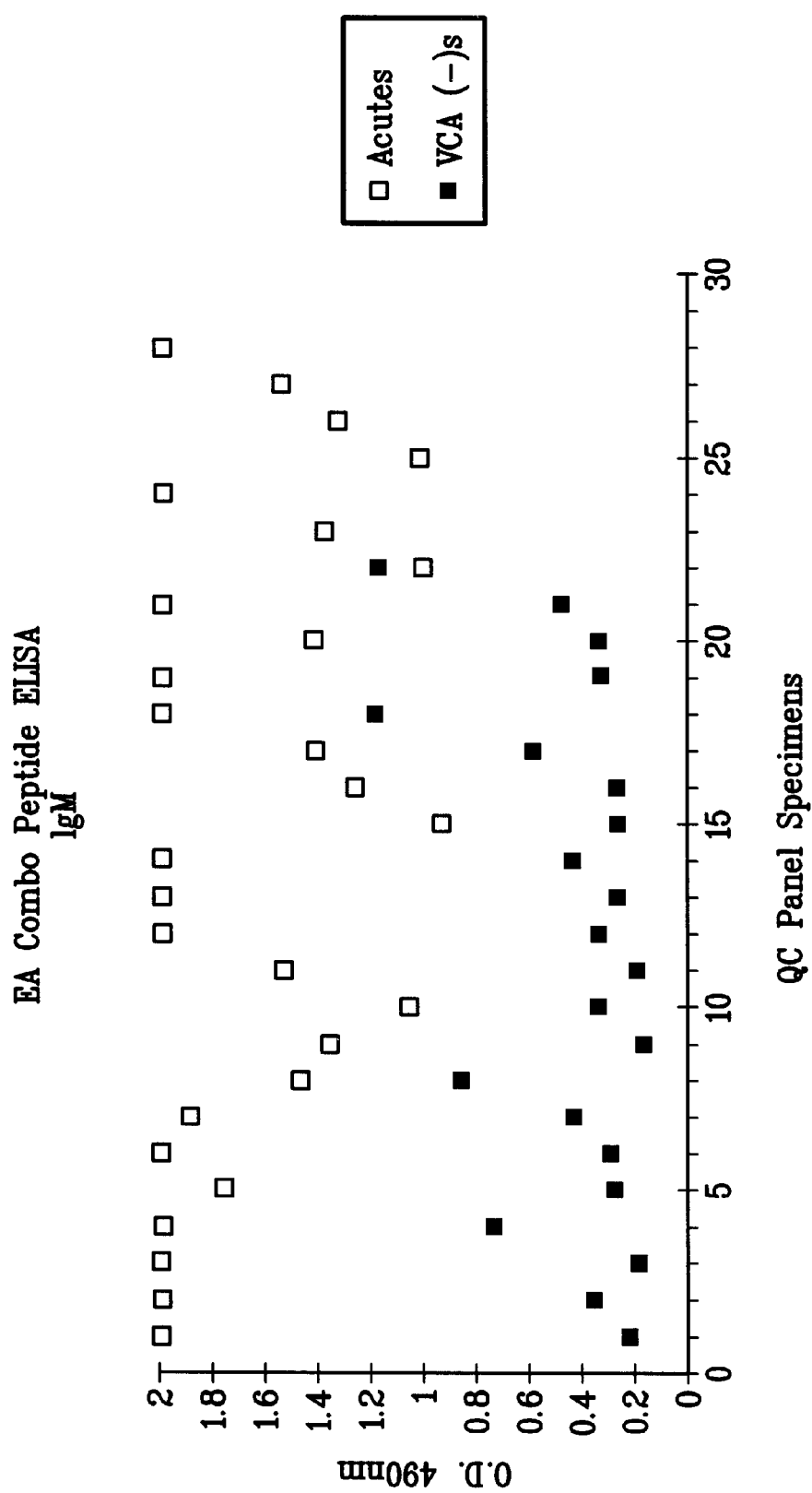
FIG. 4 shows an EA peptide combination ELISA (K7B, 50.10, 17.1). Detection of IgM antibody is shown for acute and VCA negative (control) serum.

The results with the EA-D+R assay are shown in FIGS. 3 and 4. The EA-D+R peptide assay showed better discrimination between positives and negatives than K7B peptide alone for IgM. The EA peptide combination assay scored more acute mono samples as positive and showed enhanced specificity in the VCA negative group for both isotypes.

TABLE 2

| | EA-D K7B ELISA (5 ug/200 ul/well) | | | |
|---|---|---|---|---|
| | IgG | | IgM | |
| N = 28 | O.D. | Score | O.D. | Score |
| (+) Cutoff = | >0.110 | | 0.5550 | |
| Equivocal | 0.100–0.110 | | | |
| Negative | <0.100 | | | |
| Blank (subtr.) | 0.002 | | 0.018 | |
| Acute 2241 | >2 | + | >2 | + |
| 11984 | >2 | + | >2 | + |
| 12005 | >2 | + | 1.164 | + |
| 12288 | 1.313 | + | >2 | + |
| 12409 | >2 | + | 1.254 | + |
| 12418 | >2 | + | >2 | + |
| 12498 | >2 | + | 1.889 | + |
| 12502 | >2 | + | 1.191 | + |
| 12587 | 1.750 | + | 1.101 | + |
| 12600 | 1.915 | + | 0.833 | + |
| 12611 | >2 | + | 1.747 | + |
| 12801 | >2 | + | >2 | + |
| 12828 | >2 | + | >2 | + |
| 12829 | >2 | + | 1.798 | + |
| 12836 | >2 | + | 0.775 | + |
| 12837 | 0.222 | + | 0.882 | + |

TABLE 2-continued

EA-D K7B ELISA
(5 ug/200 ul/well)

| N = 28 | IgG O.D. | Score | IgM O.D. | Score |
|---|---|---|---|---|
| 12840 | >2 | + | 1.397 | + |
| 12889 | >2 | + | >2 | + |
| 12892 | 0.766 | + | >2 | + |
| 12893 | 0.219 | + | 0.769 | + |
| 12900 | >2 | + | 1.661 | + |
| 13075 | 0.025 | − | 0.708 | + |
| 13769 | 0.044 | − | 1.138 | + |
| 13929 | 0.826 | + | >2 | + |
| 14043 | >2 | + | 0.388 | − |
| 14128 | 0.072 | − | 0.893 | + |
| 14131 | 0.371 | + | 1.164 | + |
| 14208 | 0.142 | + | >2 | + |
| % Positive: | 25/28 = 89% | | 27/28 = 96% | |

TABLE 3

EA-D 50.1 and EA-R 17.1 ELISA

| N = 33 | | EA-D p50.1 IgG | | EA-R p17.1 IgG | |
|---|---|---|---|---|---|
| Blanks | | −0.002 | | −0.001 | |
| Acute | 12288 | 0.109 | | 0.105 | |
| Negative Control | RSS | 0.124 | | 0.017 | |
| Panel Acutes: | 2241 | 0.200 | + | 0.193 | + |
| | 11984 | 0.155 | + | 0.093 | − |
| | 12005 | 0.077 | + | NA | NA |
| | 12288 | 0.089 | − | 0.107 | + |
| | 12407 | 0.071 | − | 0.105 | + |
| | 12409 | 0.214 | + | 0.082 | + |
| | 12418 | 0.182 | + | 0.098 | + |
| | 12498 | 0.142 | + | 0.124 | + |
| | 12502 | 0.292 | + | 0.169 | + |
| | 12587 | 0.127 | + | 0.048 | + |
| | 12600 | 0.028 | − | 0.030 | + |
| | 12611 | 0.061 | − | 0.089 | + |
| | 12801 | 0.102 | − | 0.094 | + |
| | 12828 | 0.449 | + | 0.144 | + |
| | 12829 | 0.068 | + | 0.042 | + |
| | 12836 | 0.835 | + | 0.688 | + |
| | 12837 | 1.724 | + | 0.080 | + |
| | 12840 | 0.376 | + | 0.020 | + |
| | 12888 | 0.142 | + | 0.131 | + |
| | 12889 | >2 | + | 0.070 | + |
| | 12892 | 0.066 | − | 0.069 | + |
| | 12893 | 0.142 | + | 0.073 | + |
| | 12899 | 0.167 | + | 0.058 | + |
| | 12900 | 0.072 | − | 0.036 | + |
| | 13075 | 0.015 | − | 0.009 | − |
| | 13419 | 0.029 | − | 0.036 | + |
| | 13637 | 0.083 | − | 0.070 | + |
| | 13769 | 0.994 | + | 0.160 | + |
| | 13929 | 0.278 | + | 0.034 | + |
| | 14043 | 0.320 | + | 0.006 | − |
| | 14128 | 0.249 | + | 0.034 | + |
| | 14131 | 0.512 | + | 0.042 | + |
| | 14208 | 0.408 | + | 0.127 | + |
| % Positive: | | 23/33 = 70% | | 30/33 = 91% | |

All OD's are adjusted so that background is zero
Anti-HuIgG-HRPO = 1/2,500 dil
Anti-HuIgM-HRPO = 1/20,000 dil
NA = not available

TABLE 4

EA-D K7B + 50.1 ELISA
(5 ug + 2.5 ug/200 ul)

| N = 33 | | IgG | | IgM | |
|---|---|---|---|---|---|
| | Blanks | 0.000 | | 0.011 | |
| Acute | 12288 | 0.959 | | 1.375 | |
| Negative Control | RSS | 0.153 | | 0.290 | |
| Panel Acutes: | 2241 | >2 | + | 1.624 | + |
| | 11984 | 1.868 | + | >2 | + |
| | 12005 | N/A | + | N/A | + |
| | 12288 | 0.818 | + | 1.272 | + |
| | 12407 | 0.102 | − | 1.050 | + |
| | 12409 | >2 | + | 1.251 | + |
| | 12418 | >2 | + | >2 | + |
| | 12498 | >2 | + | 0.838 | + |
| | 12502 | >2 | + | 1.028 | + |
| | 12587 | 1.040 | + | 0.839 | + |
| | 12600 | 2.003 | + | 0.892 | + |
| | 12611 | >2 | + | 1.321 | + |
| | 12801 | >2 | + | 1.995 | + |
| | 12828 | 1.653 | + | >2 | + |
| | 12829 | >2 | + | 1.570 | + |
| | 12836 | 2.033 | + | 0.763 | + |
| | 12837 | 1.316 | + | 0.987 | + |
| | 12840 | >2 | + | 0.849 | + |
| | 12888 | 0.196 | + | 1.003 | + |
| | 12889 | >2 | + | 1.751 | + |
| | 12892 | 0.270 | + | >2 | + |
| | 12899 | 1.051 | + | 1.125 | + |
| | 12900 | >2 | + | 0.813 | + |
| | 13075 | 0.065 | − | 1.244 | + |
| | 13419 | 0.060 | − | 0.607 | + |
| | 13637 | 0.075 | − | 0.735 | + |
| | 13769 | 0.737 | + | 0.784 | + |
| | 13929 | 1.082 | + | 1.075 | + |
| | 14043 | >2 | + | >2 | + |
| | 14128 | 0.233 | + | 0.644 | + |
| | 14131 | 0.581 | + | 0.809 | + |
| | 14208 | 0.456 | + | 1.208 | + |
| % Positive: | | 30/33 = 91% | | 33/33 = 100% | |

N/A = not available
All OD's are adjusted so that background is zero
Anti-HuIgG-HRPO = 1/2,500 dil
Anti-HuIgM-HRP0 = 1/20,000 dil

TABLE 5

K7B + 17.1 + 50.1
(5 + 0.01 + ug/200 ul/well)

| N = 28 | | IgG O.D. | Score | IgM O.D. | Score |
|---|---|---|---|---|---|
| (+) Cutoff = | | >0.110 | | 0.600 | |
| Equivocal | | 0.100–0.110 | | | |
| Negative | | <0.100 | | <0.600 | |
| Blank (subtr.) | | 0.004 | | 0.057 | |
| Acute | 2241 | >2 | + | >2 | + |
| | 11984 | 1.387 | + | >2 | + |
| | 12005 | >2 | + | >2 | + |
| | 12288 | 0.828 | + | >2 | + |
| | 12409 | >2 | + | 1.761 | + |
| | 12418 | >2 | + | >2 | + |
| | 12498 | >2 | + | 1.892 | + |
| | 12502 | >2 | + | 1.469 | + |
| | 12587 | 0.891 | + | 1.356 | + |
| | 12600 | 1.598 | + | 1.057 | + |
| | 12611 | >2 | + | 1.539 | + |
| | 12801 | >2 | + | >2 | + |
| | 12828 | 1.382 | + | >2 | + |
| | 12829 | >2 | + | >2 | + |
| | 12836 | >2 | + | 0.937 | + |
| | 12837 | 0.421 | + | 1.27 | + |
| | 12840 | >2 | + | 1.416 | + |

TABLE 5-continued

K7B + 17.1 + 50.1
(5 + 0.01 + ug/200 ul/well)

| N = 28 | IgG | | IgM | |
|---|---|---|---|---|
| | O.D. | Score | O.D. | Score |
| 12889 | >2 | + | >2 | + |
| 12892 | 0.575 | + | >2 | + |
| 12893 | 0.260 | + | 1.423 | + |
| 12900 | >2 | + | >2 | + |
| 13075 | 0.037 | − | 1.006 | + |
| 13769 | 0.261 | + | 1.379 | + |
| 13929 | 0.685 | + | >2 | + |
| 14043 | 1.757 | + | 1.017 | + |
| 14128 | 0.174 | + | 1.326 | + |
| 14131 | 0.327 | + | 1.541 | + |
| 14208 | 0.229 | + | >2 | + |
| % Positive: | 27/28 = 96% | | 28/28 = 100% | |

TABLE 6

SENSITIVITY OF EA-D AND EA-D + R PEPTIDE ELISA

| PEPTIDE ELISAS | SENSITIVITY (PERCENT POSITIVE) |
|---|---|
| HETEROPHILE POSITIVE SAMPLES | |
| K7B (IgG) | 89% |
| K7B (IgM) | 83 |
| 50.1 (IgG) | 70 |
| 17.1 (IgG) | 91 |
| K7B + 50.1 (IgG) | 91 |
| K7B + 50.1 (IgM) | 100 |
| K7B + 50.1 + 17.1 (IgG) | 86 |
| K7B + 50.1 + 17.1 (IgM) | 97 |
| WESTERN BLOT POSITIVE SAMPLES | |
| K7B (IgG) | 89% |
| K7B (IgM) | 96 |
| K7B + 50.1 + 17.1 (IgG) | 96 |
| K7B + 56.1 + 17.1 (IgM) | 100 |

Example 4

Figure 5:
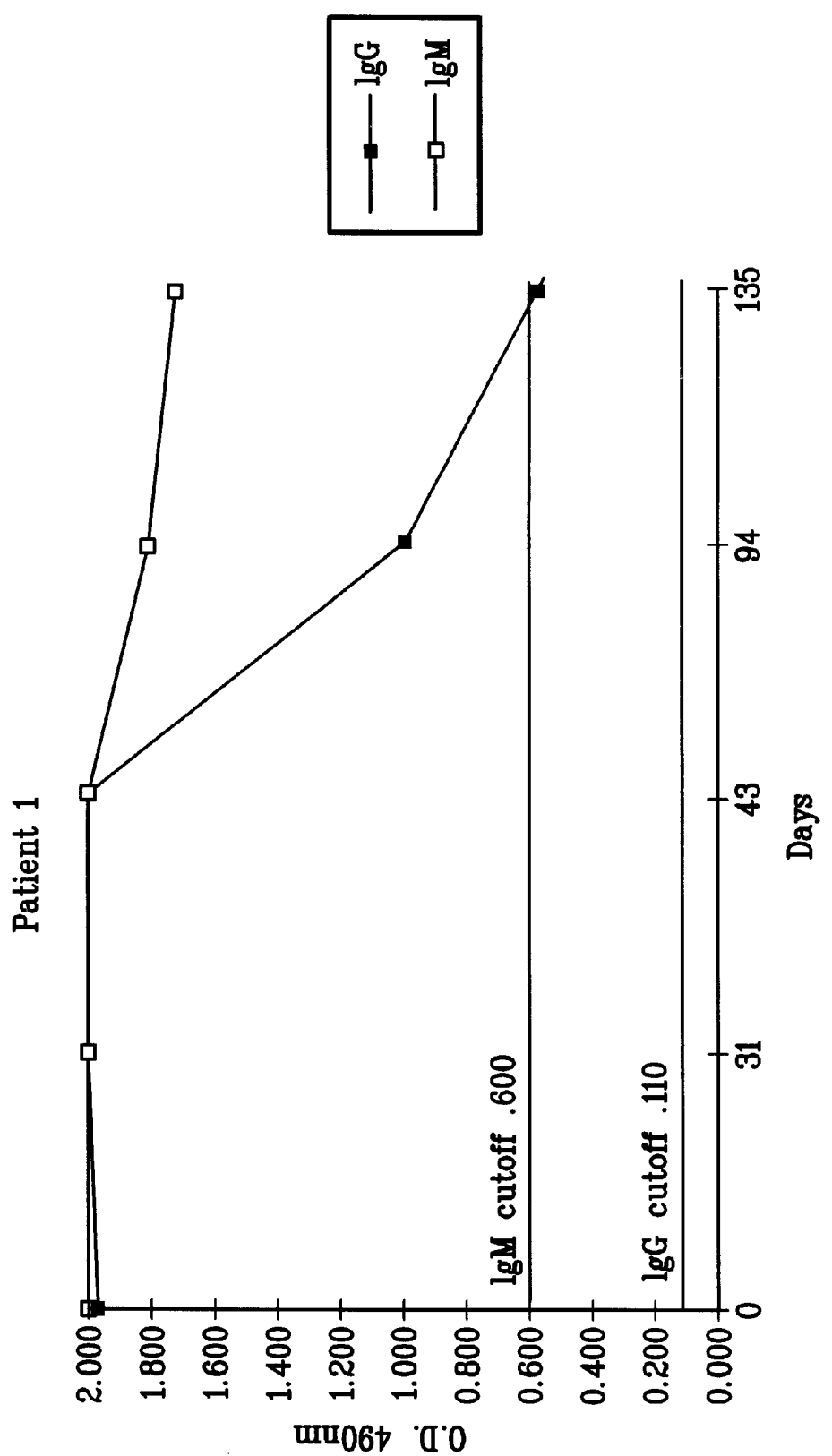
FIG. 5 shows an EA peptide combination ELISA over the course of an IM infection in a single patient. Detection of IgG and IgM antibodies is shown.

Detection of IgG and IgM Early Antigen D/R Antibody Transition in Infectious Mononucleosis The early antigen IgG and IgM transition was followed in a patient during a course of acute infectious mononucleosis. Antibodies to peptides 50.10 (EA-D), K7B (EA-D) and 17.1 (EA-R) used in combination, were detected by ELISA on specimens collected over a five month duration. The data in Table 7 and FIG. 5 show that the IgG antibodies reactive with the combination of peptides, began to decline at about 43 days, while the IgM antibodies remained at about the same level as day 0. Therefore, the peptides used in the method of invention are useful for monitoring the course of IgG and IgM antibodies independently in a patient with EBV-associated disease.

TABLE 7

COMBINATION ELISA: SEQUENTIAL IgG AND IgM SERA

| DATE | SERUM NO. | IgG | IgM |
|---|---|---|---|
| Jun. 29, 1993 (day 0) | 16809 | 1.976 | 2.000 |
| Jul. 20, 1993 (day 31) | 16811 | 2.000 | 2.000 |
| Aug. 11, 1993 (day 43) | 16978 | 2.000 | 2.000 |
| Oct. 1, 1993 (day 94) | 16989 | 1.007 | 1.819 |
| Nov. 12, 1993 (day 135) | 17235 | 0.570 | 1.741 |

Controls:
Blank 0.000 (IgG); 0.008 (IgM)
12288 0.842 (IgG); 1.509 (IgM)
Negative Control 0.290 (IgG); 0.502 (IgM)
O.D. 490 nm; sera tested at 1:20 dilution; (+) > 0.25.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

SUMMARY OF SEQUENCES

SEQ ID NO: 1 is the amino acid sequence for peptide, p50.10, from the 50.10 peptide of the diffused component of the early antigen (EA-D) of the Epstein-Barr virus (EBV).

SEQ ID NO: 2 is the amino acid sequence for peptide, K7B, from the K7B peptide of EA-D.

SEQ ID NO: 3 is the amino acid sequence for peptide, p17.1, from 17.1 peptide of the restricted component of the early antigen (EA-R) of the EBV.

What is claimed is:

1. A method for detecting antibodies which bind to a first peptide consisting essentially of the amino acid sequence KQKHPKKVKQAFNPL, or a second peptide consisting essentially of the amino acid sequence PARPETPSPAIPS, wherein the first and the second peptides bind to an antibody in a body specimen from an individual with an infectious mononucleosis (IM) disease, the method comprising the steps of:

(a) providing the first and second peptides;

(b) contacting a specimen from the individual with the peptides;

(c) incubating the specimen and the peptides for a period of time and under conditions sufficient for the antibodies to bind to the peptides; and (d) detecting the presence of the antibodies to the peptides.

2. The method of claim 1, wherein the specimen is blood.

3. The method of claim 1, wherein the detecting utilizes a detectable label.

4. The method of claim 1, wherein the label is selected from the group consisting of a radioisotope, a fluorescent compound, a colloidal metal, a chemiluminescent compound, a bioluminescent compound, a phosphorescent compound and an enzyme.

5. The method of claim 1, wherein the peptides are bound to a solid matrix support.

6. The method of claim 1, wherein the individual is a human.

7. The method of claim 1, wherein the detecting utilizes a detectably labeled protein which binds to the antibody.

8. The method of claim 7, wherein the detectably labeled protein is a detectably labeled second antibody.

9. The method of claim 8, wherein the second antibody specifically binds to an antibody of the IgG, IgM, or IgA class.

10. The method of claim 1, wherein said antibodies bind to the first peptide, or the second peptide, or a third peptide consisting essentially of the amino acid sequence ETFTETWNRFITHTEY, and wherein the body specimen of the step (b) are contacted with the first, the second and the third peptides.

11. A diagnostic kit for detecting the presence of antibodies which bind to a first peptide consisting essentially of the amino acid sequence n, or a second peptide consisting essentially of amino acid sequence n, wherein X and Y are each from 0 to 5 naturally occurring amino acids, wherein n is from 1 to 1000, and, wherein the first and second peptides bind to an antibody in a specimen from an individual with an infectious mononucleosis (IM) disease, the kit comprising a first container containing the first and second peptides and a second container containing a detectable label for detecting binding of the peptides and the antibodies.

12. The kit of claim 11, wherein the detectable label is selected from the group consisting of a radioisotope, a fluorescent compound, a colloidal metal, a chemiluminescent compound, a bioluminescent compound, a phosphorescent compound and an enzyme.

13. The kit of claim 11, wherein the detecting utilizes a detectably labeled protein which binds to the antibody.

14. The kit of claim 13, wherein the detectably labeled protein is a detectably labeled second antibody.

15. The kit of claim 14, wherein the second antibody specifically binds to an antibody of the IgG, IgA or IgM class.

16. The kit of claim 11, wherein the peptides are bound to a solid matrix.

17. The kit of claim 11, further comprising the peptide [X]ETFTETWNRFITHTE[$Y_n$].

18. The method of claim 1, wherein said amino acid sequence KQKHPKKVKQAFNPL further includes amino acids ARQ to its N-terminus, and amino acid I to its C-terminus.

19. The kit of claim 11, wherein said amino acid sequence KQKHPKKVKQAFNPL further includes amino acids ARQ to its N-terminus, and amino acid I to its C-terminus.

* * * * *

UNITED STATES PATENT AND TRADEMARK OFFICE
CERTIFICATE OF CORRECTION

| | | |
|---|---|---|
| PATENT NO. | : 6,506,553 B1 | Page 1 of 1 |
| APPLICATION NO. | : 08/413233 | |
| DATED | : January 14, 2003 | |
| INVENTOR(S) | : Smith, Richard S. and Parks, D. Elliot | |

It is certified that error appears in the above-identified patent and that said Letters Patent is hereby corrected as shown below:

In the specification:

Column 8, line 60: After "et al.," delete the letter "i".

In the claims:

Col. 17
11. A diagnostic kit for detecting the presence of antibodies which bind to a first peptide consisting essentially of the amino acid sequence ~~n~~ [[X]KQKHPKKVKQAFNPL[Y]]$_n$, or a second peptide consisting essentially of amino acid sequence ~~n~~ [[X] PARPETPSPAIPS[Y]]$_n$, wherein X and Y are each from 0 to 5 naturally occurring amino acids, wherein n is from 1 to 1000, and,
wherein the first and second peptides bind to an antibody in a specimen from an individual with an infectious mononucleosis (IM) disease, the kit comprising a
first container containing the first and second peptides and a second container containing a detectable label for detecting binding of the peptides and the antibodies.

Col. 18
17. The kit of claim 11, further comprising the peptide
~~[X]ETFTETWNRFITHTE[Yn]~~ [[X]ETFTETWNRFITHTE[Y]]$_n$.

Signed and Sealed this

Twenty-second Day of August, 2006

JON W. DUDAS
*Director of the United States Patent and Trademark Office*